(12) United States Patent
Boese et al.

(10) Patent No.: US 8,353,851 B2
(45) Date of Patent: Jan. 15, 2013

(54) APPARATUS FOR AUTOMATIC REPLACEMENT OF INSTRUMENTS DURING MINIMALLY INVASIVE PROCEDURES

(75) Inventors: Jan Boese, Eckental (DE); Reinmar Killmann, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 1731 days.

(21) Appl. No.: 11/453,611

(22) Filed: Jun. 15, 2006

(65) Prior Publication Data

US 2007/0049908 A1    Mar. 1, 2007

(30) Foreign Application Priority Data

Jun. 15, 2005    (DE) .......................... 10 2005 027 677

(51) Int. Cl.
*A61B 5/103*    (2006.01)
*A61B 5/117*    (2006.01)

(52) U.S. Cl. ...................................................... 600/587
(58) Field of Classification Search ................. 600/585, 600/587; 604/48, 93.01, 95.01
See application file for complete search history.

(56) References Cited

U.S. PATENT DOCUMENTS

| | | |
|---|---|---|
| 5,871,495 A | 2/1999 | Mueller |
| 6,015,414 A | 1/2000 | Werp et al. |
| 6,109,270 A | 8/2000 | Mah et al. |
| 2004/0044350 A1* | 3/2004 | Martin et al. ................. 606/139 |

FOREIGN PATENT DOCUMENTS

| | | |
|---|---|---|
| JP | 2005502441 A | 1/2005 |
| WO | WO 02/089872 A2 | 11/2002 |

* cited by examiner

*Primary Examiner* — Jeffrey G Hoekstra

(57) ABSTRACT

The invention relates to an apparatus for automatic replacement of instruments during minimally invasive procedures, comprising a housing, an outlet element for an instrument, a selection unit and a guide element.

7 Claims, 1 Drawing Sheet

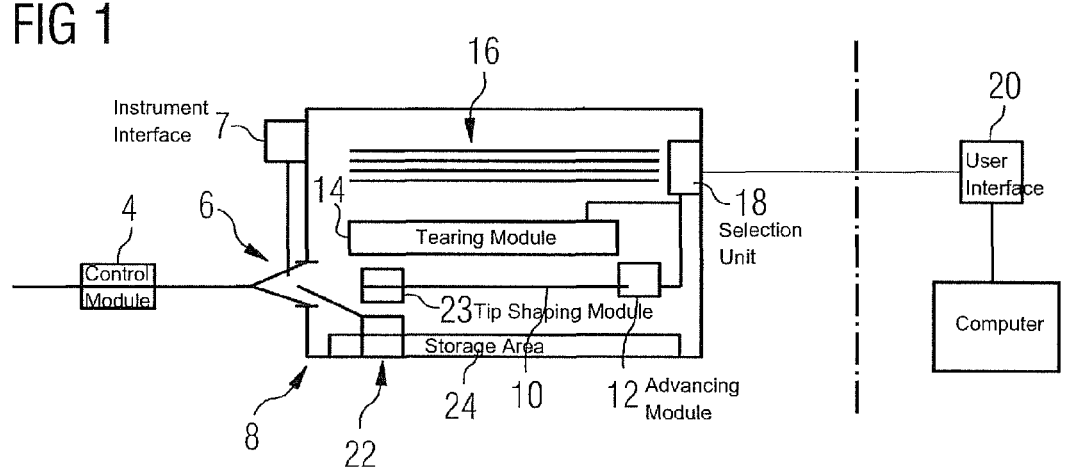
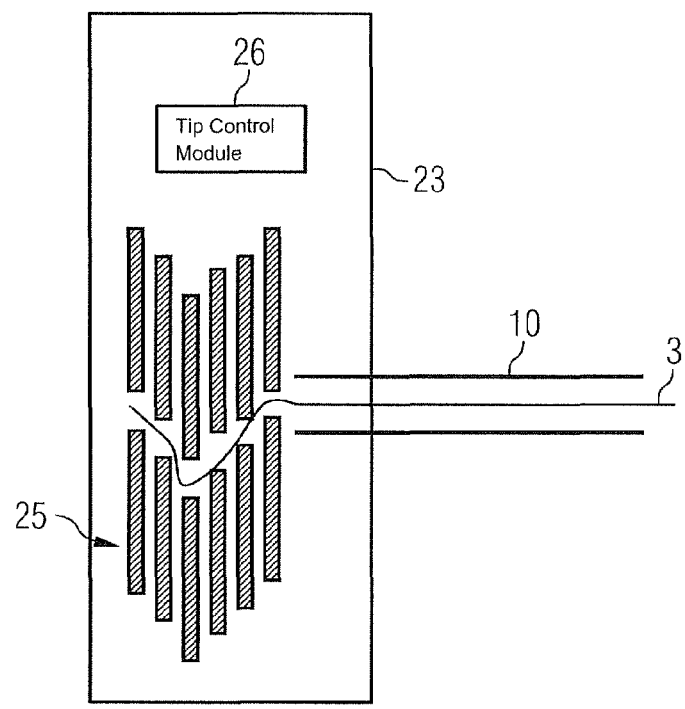

APPARATUS FOR AUTOMATIC REPLACEMENT OF INSTRUMENTS DURING MINIMALLY INVASIVE PROCEDURES

CROSS REFERENCE TO RELATED APPLICATIONS

This application claims the benefits of German Patent application No. 10 2005 027 677.6 filed Jun. 15, 2005 and is incorporated by reference herein in its entirety.

FIELD OF THE INVENTION

The invention relates to an apparatus for automatic replacement of instruments during minimally invasive procedures, comprising a housing, an outlet element for an instrument, a selection unit and a guide element.

BACKGROUND OF THE INVENTION

Interventions in the human body are increasingly performed using minimally invasive methods instead of surgical operations. Said minimally invasive interventions, also referred to as interventional procedures, are frequently employed for treating vascular diseases.

In said procedures the first step is to introduce what is referred to as a guide wire, which serves to probe the lumina, e.g. the interior of blood vessels. Via a guide wire of said kind it is then possible to introduce further instruments, such as, for instance, catheters, endoscopes, placement instruments (e.g. for placing stents, balloons, etc.), dilatation instruments or the like, to the desired position. When swapping between a plurality of instruments, such as e.g. a catheter and a placement instrument, the guide wire is usually withdrawn for each change and reintroduced.

This procedure is illustrated in the following using the example of an intervention for treating a myocardial infarction:
Access to a peripheral artery, e.g. in the groin area, is created with the aid of a puncture.
What is referred to as an introducer sheath is then introduced via this access and advanced as far as the area of the aortic arch.
What is referred to as a guide wire is inserted via said introducer sheath and is then used to probe the outlets of the coronary arteries from the aorta. The guide wire is then introduced into the coronary arteries.
A catheter with an inner lumen is then pushed into the coronary artery via the guide wire.
The guide wire is removed and contrast medium injected into the coronary artery via the lumen of the catheter. The course of the coronary vessels is rendered visible by means of simultaneous real-time x-ray imaging, thereby visualizing a possible constriction of the vessels (stenosis, incipient myocardial infarction).
The guide wire is now reintroduced via the lumen of the catheter and advanced to the point in the coronary vasculature at which the constriction was visible.
The following three operating steps are optional:
The lumen catheter is removed and a balloon dilatation instrument is pushed to the constricted point via the guide wire.
The guide wire is withdrawn again.
The balloon introduced into the coronary vessel is inflated up to as high as 20 bar, thus expanding (dilating) the vessel. The pressure is then released again.
The guide wire is reintroduced into the vessel.
The balloon dilatation instrument is withdrawn and removed from the body.
A stent placement instrument is introduced via the guide wire. Said instrument guides a framework (stent) consisting of metal wires to the formerly constricted point and is inflated there (similarly to the previously described balloon dilatation procedure). The stent is detached from the placement instrument and remains in the body. Its function is to prevent a re-narrowing (restenosis) of the vessel.
Stent placement instrument and guide wire are withdrawn from the body.

With reference to the workflow for coronary intervention this example shows that instruments that are introduced frequently have to be changed.

Currently, the instruments are changed manually, the person carrying out the intervention making the appropriate replacement.

In fact there already exist automated methods wherein the instruments are controlled by remote control. An example of this is magnetic navigation, as provided by the company Stereotaxis Inc. (see U.S. Pat. No. 6,015,414). In that case what is termed a "catheter advancing system", as described in WO 02/089872 A2, is used for advancing the catheter. Here, the person carrying out the intervention, e.g. the physician, is able to control the movement of the instruments in the body of the person to be examined remotely from the control room. However, only one instrument at a time can be used in a catheter advancing system of said kind. Each time the instruments are changed, the person carrying out the intervention must therefore enter the examination room. Considerable disadvantages are associated with this. Apart from the time lost on account of the distance to be covered, other risks also ensue, such as e.g. a risk of contamination due to the need to change between non-sterile environment and sterile environment.

SUMMARY OF THE INVENTION

The object of the present invention was therefore to provide an apparatus which eliminates at least some of the cited disadvantages of the prior art.

According to the invention an apparatus for automatic replacement of instruments during minimally invasive procedures is therefore proposed, said apparatus comprising a housing, an outlet element for an instrument, a selection unit for selecting an instrument, a guide element, and a graphical user interface connected to the selection unit.

The apparatus according to the invention is suitable as an automatic instrument changer and is preferably used for remote-controlled and/or automated minimally invasive interventions in order to perform the replacement of the instruments automatically or by remote control.

The apparatus according to the invention firstly comprises a housing. The housing contains the cited elements and serves to accommodate and make available the instruments that are to be used. The housing can have any suitable shape.

The instruments are instruments that are provided for use in the body of a person who is to be examined. For example, the instrument can be what is referred to as a guide wire which serves to probe the vascular cavities. However, the instruments may also be catheters or endoscopes or what are termed placement elements, such as e.g. stent placement elements, or dilatation instruments, such as e.g. a balloon dilatation instrument. These types of instruments for minimally invasive interventions are sufficiently known to the person skilled in the art and each of said instruments can be used in the apparatus according to the invention.

The apparatus according to the invention also includes an outlet element. This is located on the housing and forms an outlet for the instrument to be used in each case. The outlet element is preferably replaceable by sterile means. The outlet element is preferably cone-shaped and in this case is preferably a cone which can be replaced by sterile means.

The apparatus further comprises a selection unit. This is contained in the interior of the housing and serves for selecting an instrument that is to be used and for placing said instrument onto a guide element. The selection unit is suitable for selecting an instrument that is to be used from the interior of the housing and for placing said instrument onto the guide element so that the instrument can be guided to the outlet element. From there it can be introduced into the body of the person that is to be examined.

The guide element can be embodied for example as a guide rail or as any other guide element. On the guide element the selected instrument, placed there by the selection unit, is guided to the outlet element. The guide element also serves for returning an instrument after use.

In this way instruments can be swapped in the interior of the apparatus, the selection unit being used to select the desired instruments. All these operations can be automated via the selection unit.

The selection unit is connected to a user interface at which the person carrying out the examination, e.g. the physician, can select the instrument that is to be used. The user interface is preferably connected to a computing unit, e.g. a computer. The user interface can also be implemented as a computer. The user interface comprises a graphical interface, e.g. a monitor.

In a preferred embodiment the apparatus according to the invention additionally has a control module for controlling an instrument. The control module is preferably located outside the housing. A control module of said type is used to control the instrument or instruments in the body of the person that is to be examined. Control modules of said type are known in the prior art. In principle any known control module can be used for the apparatus according to the invention. The control module is preferably based on magnetic navigation. A particularly preferred control module is therefore a magnetic navigation system, as disclosed, for example, in U.S. Pat. No. 6,015,414. This includes what is referred to as a catheter advancing system (WO02/089872 A2). Such a system is used for automatically controlling and moving catheters and other elongate minimally invasive instruments in the body of a subject. By means of a catheter advancing system of said type an instrument can be advanced and retracted in the body, and also controlled, by remote control.

The apparatus according to the invention can additionally comprise a separate advancing module which can, if necessary, be connected to the selection unit and/or the guide element. Once an instrument has been selected and placed on the guide element, the advancing module can move the instrument in the direction of the outlet element. The advancing element can also be used in order to retract an instrument again.

In a preferred embodiment a retracting device can additionally be provided for the purpose of removing instruments after use. The retracting device can be implemented for example as a gripper device. By this means instruments that are no longer to be used can be withdrawn from the outlet element and discarded or else stored in a storage area for used instruments. The instruments can also continue to be held in readiness for reuse.

The apparatus preferably includes a storage area for storing instruments. The instruments can be stored there in their (preferably sterile) packaging until they are to be used.

In the case of packaged instruments the apparatus according to the invention preferably includes an unpacking device which only releases the selected instrument from its sterile packaging shortly before use. The unpacking device can be suitably embodied for tearing open the packaging.

Preferably the apparatus according to the invention additionally includes an instrument interface. The instrument interface enables the automatic establishment of connections of the instrument to other devices. For example, it sets up automatic connections to contrast medium pumps and pressure generators. Thus, for example, a balloon catheter can be blown up to a specific pressure by remote control. Injections of contrast medium and sodium chloride solution are likewise possible by remote control. The useful connections are established automatically for each selected instrument and injection parameters are proposed. The instrument interface also allows the remotely controlled and instrument-specific establishment of connections to other systems, for example for rotablation instruments, pressure measurement wires, IVUS catheters, OCT catheters or electrophysiology catheters.

In a further preferred embodiment the apparatus according to the invention includes a tip shaping module. This can be used to give instruments, in particular guide wires, a specific tip shape by remote control. Said shape can, for example, be defined beforehand at the user interface. In order to apply the tip shape the instrument is inserted, prior to its introduction into the patient, into the tip shaping module, which is preferably located at the end of the guide rail. The tip shaping module preferably comprises a tip control module, the latter preferably including a plurality of shaping elements which are preferably present in the form of lamellae. The desired tip shape is preferably applied by means of lamellae that are movable under computer control. Optionally, the match with the planned tip shape is measured by the tip control module (e.g. by laser sampling of the instrument tip) and improved in an iterative process.

The sterility of the instruments is preferably ensured by means of replaceable units of the apparatus according to the invention, e.g. a replaceable sterile cone, replaceable guide rail and a replaceable advancing module. The latter can be embodied, for example, in the form of the catheter advancer system from the company Stereotaxis.

The advantage that is produced by this invention lies in the totally remotely controllable procedure, e.g. in magnetic navigation from the company Stereotaxis. This possibility of remote control is a step toward automatable procedures. Advantages for the physician are savings in terms of time and distance and reduced exposure to radiation.

As far as the patient is concerned, the invention results in the advantage that the duration of the treatment is shortened and the risk of infection reduced due to the avoidance of manual handling of the instruments. Moreover, thanks to the fast replaceability of instruments new procedures could be developed which for reasons of practicability are not possible at the present time due to frequent changes of instruments.

BRIEF DESCRIPTION OF THE DRAWINGS

With reference to the accompanying drawings, a preferred embodiment of the invention will now be described. The drawings show:

FIG. 1 a schematic representation of an apparatus according to the invention, and FIG. 2 a schematic representation of a tip shaping module.

DETAILED DESCRIPTION OF THE INVENTION

FIG. 1 shows a schematic diagram of an exemplary embodiment of an apparatus according to the invention. In this arrangement the instrument 2 introduced into the body of the patient is controlled via a control and advancing module 4 (e.g. Stereotaxis magnetic navigation system in combination with the Stereotaxis catheter advancer system).

The apparatus 8 contains a replaceable, sterile cone 6 which enables a precise adjustment and fit of the instrument that is to be introduced (e.g. guide wire or catheter or the like). Also included is a guide rail 10 on which the instrument that is to be newly introduced is advanced with the aid of the advancing module 12. The sterilely packaged instruments can be stored in the depot 16, the packaging being removed in the tearing module 14 before the instrument is placed onto the guide rail 10.

An instrument interface 7 enables the automatic establishment of connections of the instrument to other devices.

The instrument that is to be introduced is selected via the user interface 20 which can be implemented e.g. on a PC. The selection unit 18 is controlled from said user interface, with the result that the selected instrument is placed onto the guide rail 10.

When an instrument is changed, the instrument that is to be removed from the body is removed from the body by means of the retracting device 22 and can be temporarily stored in the storage area 24 for already used instruments.

In a preferred embodiment the system can be equipped e.g. with two different storage areas. Instruments that are to be reintroduced into the body later can be stored in one area, while instruments that will no longer be introduced into the body in the further course of the procedure can be stored in the other storage area.

FIG. 2 shows an optional tip shaping module 23. This can be used to give guide wires a specific tip shape by remote control. Said tip shape is defined beforehand at the user interface 20. In order to apply the tip shape, before being introduced into the patient the instrument is inserted into the tip shaping module which is located at the end of the guide rail 10. There, the shape is applied by means of lamellae 25 that are movable under computer control. Optionally, the match with the planned tip shape is measured by the tip control module 26 (e.g. by laser sampling of the instrument tip) and improved in an iterative process.

The invention claimed is:

1. An apparatus for automatic replacement of medical instruments during a minimally invasive medical procedure, comprising:
   a housing that contains a plurality of medical instruments;
   a replaceable outlet element arranged on the housing that forms an outlet for the plurality of medical instruments and configured to allow one of the plurality of medical instruments to pass through the housing;
   a selection unit contained in an interior of the housing for selecting a selected instrument;
   a guide element arranged in the interior of the housing that guides the selected instrument to the outlet element and returns the selected instrument after use;
   a graphical user interface connected to the selection unit that interfaces with a human performing the medical procedure to select the selected instrument; and
   a tip shaping module located at a distal end of the guide element that shapes a tip of the selected instrument.

2. The apparatus as claimed in claim 1, wherein the instrument is a guide wire.

3. The apparatus as claimed in claim 1, wherein the tip shaping module is a tip control module.

4. The apparatus as claimed in claim 3, wherein the tip control module comprises a plurality of shaping elements.

5. The apparatus as claimed in claim 4, wherein the shaping elements comprise lamellae.

6. The apparatus as claimed in claim 5, wherein the tip shape is controlled by a computer.

7. The apparatus as claimed in claim 6, wherein an intended tip shape is compared to an actual tip shape and the actual tip shape is modified by the shaping element to improve the intended tip shape.

\* \* \* \* \*